(12) United States Patent
Kostrzewski et al.

(10) Patent No.: US 10,292,778 B2
(45) Date of Patent: *May 21, 2019

(54) SURGICAL INSTRUMENT HOLDER FOR USE WITH A ROBOTIC SURGICAL SYSTEM

(71) Applicant: KB MEDICAL, SA, Audubon, PA (US)

(72) Inventors: Szymon Kostrzewski, Lausanne (CH); Billy Nussbaumer, Boudry (CH)

(73) Assignee: Globus Medical, Inc., Audubon, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/990,910

(22) Filed: May 29, 2018

(65) Prior Publication Data

US 2018/0271605 A1    Sep. 27, 2018

Related U.S. Application Data

(63) Continuation of application No. 14/695,154, filed on Apr. 24, 2015, now Pat. No. 10,004,562.

(60) Provisional application No. 61/983,816, filed on Apr. 24, 2014.

(51) Int. Cl.
*B25B 27/14* (2006.01)
*A61B 34/30* (2016.01)
*A61B 34/00* (2016.01)
*A61B 17/00* (2006.01)
*A61B 90/00* (2016.01)

(52) U.S. Cl.
CPC .............. *A61B 34/30* (2016.02); *A61B 34/70* (2016.02); *A61B 2017/00464* (2013.01); *A61B 2017/00477* (2013.01); *A61B 2090/3983* (2016.02)

(58) Field of Classification Search
USPC .............................. 29/281.5; 606/1, 99, 130
See application file for complete search history.

(56) References Cited

U.S. PATENT DOCUMENTS

| | | |
|---|---|---|
| 4,150,293 A | 4/1979 | Franke |
| 5,246,010 A | 9/1993 | Gazzara et al. |
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |

(Continued)

OTHER PUBLICATIONS

US 8,231,638 B2, 07/2012, Swarup et al. (withdrawn)

*Primary Examiner* — Joseph J Hail
*Assistant Examiner* — Shantese McDonald

(57) ABSTRACT

Described herein is a surgical instrument holder for use with a robotic surgical system, for example, during spinal surgery. In certain embodiments, the surgical instrument holder is an interface between the robotic arm and a surgical instrument used during surgery. This interface may hold the surgical instrument precisely, rigidly, and in a stable manner while permitting a surgeon to easily and quickly install or withdraw the instrument in case of emergency.

20 Claims, 16 Drawing Sheets

(56) References Cited

U.S. PATENT DOCUMENTS

| | | |
|---|---|---|
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |

(56) References Cited

U.S. PATENT DOCUMENTS

| | | |
|---|---|---|
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,263,933 B2 | 9/2012 | Zeile |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |

(56) References Cited

U.S. PATENT DOCUMENTS

| | | |
|---|---|---|
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0161136 A1* | 7/2006 | Anderson .............. A61B 90/57 606/1 |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2007/0299427 A1* | 12/2007 | Yeung ................ B25J 9/047 606/1 |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |

(56) References Cited

U.S. PATENT DOCUMENTS

| | | |
|---|---|---|
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0166496 A1* | 7/2010 | Bennett ............ A61B 17/32002 403/122 |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |

(56) References Cited

U.S. PATENT DOCUMENTS

| | | |
|---|---|---|
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucker et al. |

\* cited by examiner

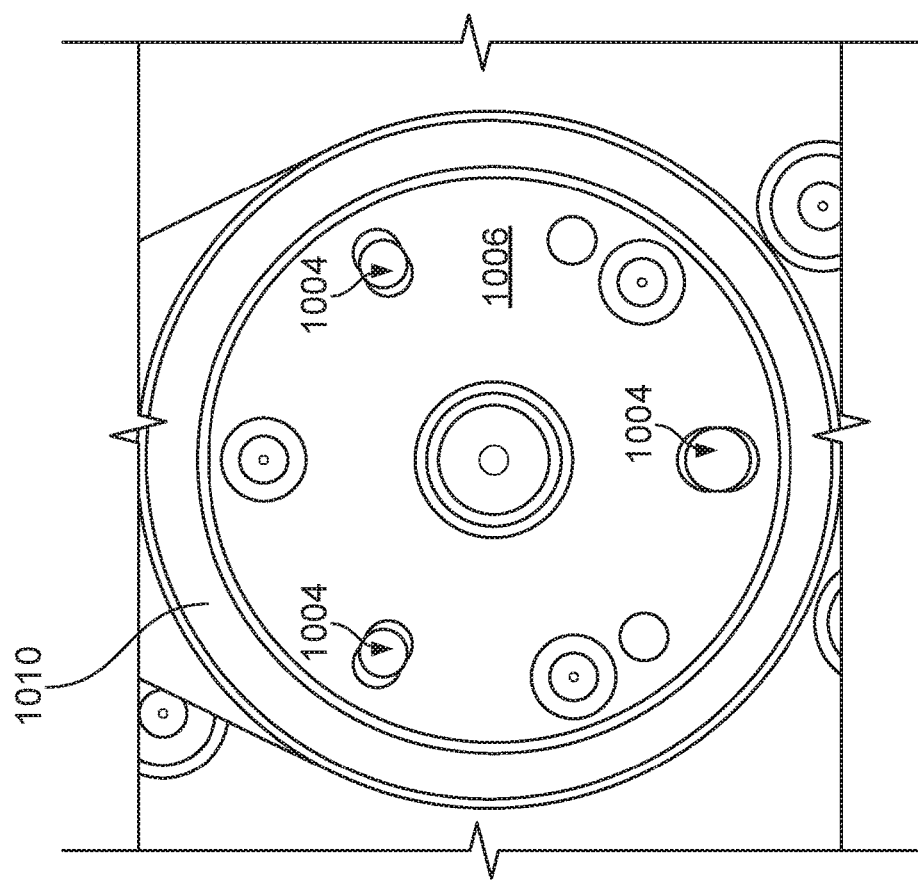

SURGICAL INSTRUMENT HOLDER FOR USE WITH A ROBOTIC SURGICAL SYSTEM

CROSS REFERENCE TO RELATED APPLICATIONS

This application is continuation of U.S. patent application Ser. No. 14/695,154, filed Oct. 29, 2015, which claims priority to U.S. provisional Application No. 61/983,816, filed Apr. 24, 2014, in which the entire contents are incorporated by reference herein in their entities for all purposes.

BACKGROUND

Robotic-assisted surgical systems have been developed to improve surgical precision and enable the implementation of new surgical procedures. For example, robotic systems have been developed to sense a surgeon's hand movements and translate them to scaled-down micro-movements and filter out unintentional tremors for precise microsurgical techniques in organ transplants, reconstructions, and minimally invasive surgeries. Other robotic systems are directed to telemanipulation of surgical tools such that the surgeon does not have to be present in the operating room, thereby facilitating remote surgery. Feedback-controlled robotic systems have also been developed to provide smoother manipulation of a surgical tool during a procedure than could be achieved by an unaided surgeon.

However, widespread acceptance of robotic systems by surgeons and hospitals is limited for a variety of reasons. Current systems are expensive to own and maintain. They often require extensive preoperative surgical planning prior to use, and they extend the required preparation time in the operating room. They are physically intrusive, possibly obscuring portions of a surgeons field of view and blocking certain areas around the operating table, such that a surgeon and/or surgical assistants are relegated to one side of the operating table. Current systems may also be non-intuitive or otherwise cumbersome to use, particularly for surgeons who have developed a special skill or "feel" for performing certain maneuvers during surgery and who find that such skill cannot be implemented using the robotic system. Finally, robotic surgical systems may be vulnerable to malfunction or operator error, despite safety interlocks and power backups.

Spinal surgeries often require precision drilling and placement of screws or other implements in relation to the spine, and there may be constrained access to the vertebrae during surgery that makes such maneuvers difficult. Catastrophic damage or death may result from improper drilling or maneuvering of the body during spinal surgery, due to the proximity of the spinal cord and arteries. Common spinal surgical procedures include a discectomy for removal of all or part of a disk, a foraminotomy for widening of the opening where nerve roots leave the spinal column, a laminectomy for removal of the lamina or bone spurs in the back, and spinal fusion for fusing of two vertebrae or vertebral segments together to eliminate pain caused by movement of the vertebrae.

Spinal surgeries that involve screw placement require preparation of holes in bone (e.g., vertebral segments) prior to placement of the screws. Where such procedures are performed manually, in some implementations, a surgeon judges a drill trajectory for subsequent screw placement on the basis of pre-operative CT scans. Other manual methods which do not involve usage of the pre-operative CT scans, such as fluoroscopy, 3D fluoroscopy or natural landmark-based, may be used to determine the trajectory for preparing holes in bone prior to placement of the screws. In some implementations, the surgeon holds the drill in his hand while drilling, and fluoroscopic images are obtained to verify if the trajectory is correct. Some surgical techniques involve usage of different tools, such as a pedicle finder or K-wires. Such procedures rely strongly on the expertise of the surgeon, and there is significant variation in success rate among different surgeons. Screw misplacement is a common problem in such surgical procedures.

Image-guided spinal surgeries involve optical tracking to aid in screw placement. However, such procedures are currently performed manually, and surgical tools can be inaccurately positioned despite virtual tracking. A surgeon is required to coordinate his real-world, manual manipulation of surgical tools using images displayed on a two dimensional screen. Such procedures can be non-intuitive and require training, since the surgeon's eye must constantly scan both the surgical site and the screen to confirm alignment. Furthermore, procedural error can result in registration inaccuracy of the image-guiding system, rendering it useless, or even misleading. Thus, there is a need for a system for stabilizing surgical instruments while allowing the instruments and the instrument holder to be both easily sterilized and installed and removed from the robotic system without deteriorating localization precision as well as attachment rigidity.

SUMMARY

Described herein is a surgical instrument holder for use with a robotic surgical system, for example, during spinal surgery. In certain embodiments, the holder is attached to a robotic arm and provides a rigid structure that allows for precise preparation of patient tissue (e.g., preparation of a pedicle) by drilling, tapping, or other manipulation, as well as precise placement of a screw in a drilled hole or affixation of a prosthetic or implant in a prepared patient situation.

In certain embodiments, the surgical instrument holder is an interface between the robotic arm and a surgical instrument used during surgery. The surgical instrument holder holds the surgical instrument precisely, rigidly, and in a stable manner while permitting a surgeon to easily and quickly install or withdraw the instrument in case of emergency. The surgical instrument includes a base that is mechanically coupled to the robotic arm.

In some implementations, the instrument holder needs to be sterilized (e.g., in autoclave). The disclosed instrument holder may be easily installed and removed from the robotic system without deteriorating localization precision as well as attachment rigidity. Localization precision is achieved by, for example, localization pins inserted into the base. The pins may come in contact with oblong openings in a thin localization plate precisely held on the robotic arm. The instrument holder's base is localized on the robotic arm using pins that come in contact with oblong openings in the localization plate. A screw may be tightened directly into the robot to rigidly attached the instrument holder's base to the robot.

A surgical instrument slides into a channel in the base of the instrument holder. A clamp may be positioned with the instrument between the base and the clamp such that the instrument is securely held between the base and the clamp when a nut is tightened against the clamp (e.g., pushing the clamp against the instrument). A navigation marker may also be secured between the base and the clamp. The surface of the clamp that contacts the nut may be cambered such that a horizontal line of contact is formed instead of a full surface. This horizontal line of contact allows the clamp to slightly tilt to accommodate for dimensional variations.

The disclosed technology, in certain embodiments, includes a surgical instrument holder for use with a robotic surgical system. The surgical instrument holder, in certain embodiments, includes a base configured to be mechanically coupled to a robotic arm of the robotic surgical system. The base may include a first channel having an interior surface sized and shaped to accommodate a tightening screw configured to securely attach the base directly or indirectly to a robotic arm of the robotic surgical system, a second channel having an interior surface with a tapered cylindrical shape sized to accommodate a surgical instrument therethrough such that movement of the surgical instrument is constrained in all directions except along an axis defined by the second channel surface, a first tapered curved surface extending along the axis of the second channel configured to be engaged by a surgical instrument when the surgical instrument is secured in the second channel, wherein first channel and the second channel intersect, and one or more pins inserted into the base such that the one or more pins (e.g., three pins), upon mechanically coupling the base to the robotic arm, engage one or more openings (e.g., one or more oblong openings) in a tool support (e.g., in a localization plate of the robotic arm) thereby precisely locating the surgical instrument holder relative to the robotic arm (e.g., where the one or more openings are wider than the one or more pins and the one or more openings taper long their lengths).

The surgical instrument holder, in certain embodiments, includes a clamp configured to engage the surgical instrument when placed through the second channel such that the surgical instrument is securely held between the clamp and the base upon tightening of a nut. The clamp may include a third channel having an interior surface shaped and sized to accommodate the first channel sliding therethrough; a second tapered curved surface configured to be engaged by a surgical instrument when the surgical instrument is secured in the second channel; and one or more slits configured to allow a body of the clamp to elastically deform upon tightening of the nut, wherein the nut is configured to engage threads on an exterior surface of the first channel and a cambered surface of the clamp. The instrument holder may be configured such that a navigation marker is securely held between the clamp the base upon placing the navigation marker between the clamp and the base and tightening the nut. In certain embodiments, the navigation marker is used by a navigation camera to track the surgical instrument.

An exterior surface of the first channel may be threaded to securely accommodate the nut such that surgical instrument is securely held between the clamp the base upon placing the surgical instrument in the second channel and tightening the nut. In certain embodiments, the surgical instrument is an instrument guide (e.g., drill guide) configured to receive a second surgical instrument therethrough, the second surgical instrument being a drill bit, tap, screw driver, or awl.

In certain embodiments, the base includes a threaded bushing having an interior surface. In certain embodiments, the first channel passes through interior surface of the threaded bushing and the interior surface of the threaded bushing is threaded such that the threads on the tightening screw engage the threads on the threaded bushing as the tightening screw is inserted through the threaded bushing. In certain embodiments, the tightening screw includes a tip on a proximate end of a screw body; a head on a distal end of the screw body; and threads along a portion of the screw body. In certain embodiments, the threads along the portion of the screw body are along a portion of the screw body closest to the tip of the tightening screw. In certain embodiments, the portion of the screw body closest to the head is smooth such that the tightening screw is loosely held in place by the threaded bushing when the tightening screw is fully inserted into the threaded bushing.

In certain embodiments, the disclosed technology includes a surgical instrument holder for use with a robotic surgical system, the surgical instrument holder including: a base configured to be mechanically coupled to a robotic arm of the robotic surgical system, the base including: a first channel having an interior surface sized and shaped to accommodate a tightening screw configured to securely attach the base directly or indirectly to a robotic arm of the robotic surgical system, a second channel having an interior surface with a tapered cylindrical shape sized to accommodate a surgical instrument therethrough such that movement of the surgical instrument is constrained in all directions except along an axis defined by the second channel surface, a first tapered curved surface extending along the axis of the second channel configured to be engaged by a surgical instrument when the surgical instrument is secured in the second channel, wherein first channel and the second channel intersect, and one or more pins inserted into the base such that the one or more pins, upon mechanically coupling the base to the robotic arm, engage one or more openings in a tool support thereby precisely locating the surgical instrument holder relative to the robotic arm; and a clamp configured to engage the surgical instrument when placed through the second channel such that the surgical instrument is securely held between the clamp and the base upon tightening of a nut.

In certain embodiments, the base includes a threaded bushing having an interior surface.

In certain embodiments, the first channel passes through interior surface of the threaded bushing and the interior surface of the threaded bushing is threaded such that the threads on the tightening screw engage the threads on the threaded bushing as the tightening screw is inserted through the threaded bushing.

In certain embodiments, the tightening screw includes: a tip on a proximate end of a screw body; a head on a distal end of the screw body; and threads along a portion of the screw body.

In certain embodiments, the threads along the portion of the screw body are along a portion of the screw body closest to the tip of the tightening screw.

In certain embodiments, the portion of the screw body closest to the head is smooth such that the tightening screw is loosely held in place by the threaded bushing when the tightening screw is fully inserted into the threaded bushing.

In certain embodiments, the clamp includes a third channel having an interior surface shaped and sized to accommodate the first channel sliding therethrough; a second tapered curved surface configured to be engaged by a surgical instrument when the surgical instrument is secured in the second channel; and one or more slits configured to allow a body of the clamp to elastically deform upon tightening of the nut, wherein the nut is configured to engage threads on an exterior surface of the first channel and a cambered surface of the clamp.

In certain embodiments, the one or more openings are one or more oblong openings.

In certain embodiments, the one or more pins comprise three pins.

In certain embodiments, the surgical instrument is an instrument guide configured to receive a second surgical instrument therethrough, the second surgical instrument comprising a member selected from the group consisting of: a drill bit, tap, screw driver, and awl.

In certain embodiments, the instrument guide is a drill guide.

In certain embodiments, the robotic surgical system is for use in spinal surgery.

In certain embodiments, instrument holder is configured such that a navigation marker is securely held between the clamp the base upon placing the navigation marker between the clamp and the base and tightening the nut.

In certain embodiments, the navigation marker is used by a navigation camera to track the surgical instrument.

In certain embodiments, the tool support is a localization plate of the robotic arm.

In certain embodiments, the one or more openings are wider than the one or more pins and the one or more openings taper long their lengths.

In certain embodiments, an exterior surface of the first channel is threaded to securely accommodate the nut such that surgical instrument is securely held between the clamp the base upon placing the surgical instrument in the second channel and tightening the nut.

BRIEF DESCRIPTION OF THE FIGURES

The foregoing and other objects, aspects, features, and advantages of the present disclosure will become more apparent and better understood by referring to the following description taken in conjunction with the accompanying drawings, in which:

FIGS. 10A-B are illustrations of a system for securing the instrument holder on the robotic arm;

Figure 1:
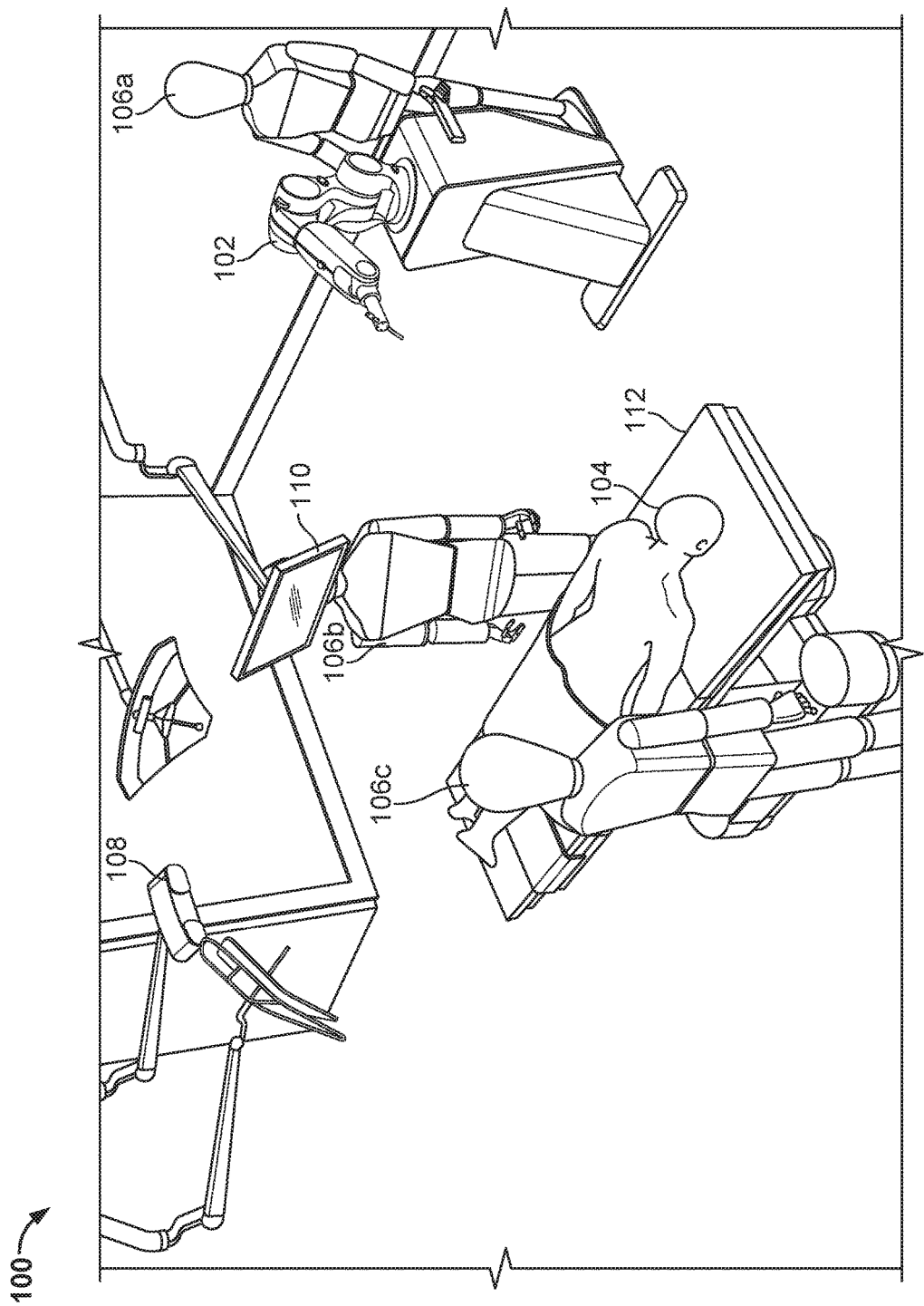
FIG. 1 is an illustration of an example robotic surgical system in an operating room.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

FIG. 1 illustrates an example robotic surgical system in an operating room 100. In some implementations, one or more surgeons, surgical assistants, surgical technologists and/or other technicians, (106a-c) perform an operation on a patient 104 using a robotic-assisted surgical system. In the operating room the surgeon may be guided by the robotic system to accurately execute an operation. This may be achieved by robotic guidance of the surgical tools, including ensuring the proper trajectory of the tool (e.g., drill or screw). In some implementations, the surgeon defines the trajectory intra-operatively with little or no pre-operative planning. The system allows a surgeon to physically manipulate the tool holder to safely achieve proper alignment of the tool for performing crucial steps of the surgical procedure. Operation of the robot arm by the surgeon (or other operator) in force control mode permits movement of the tool in a measured, even manner that disregards accidental, minor movements of the surgeon. The surgeon moves the tool holder to achieve proper trajectory of the tool (e.g., a drill or screw) prior to operation or insertion of the tool into the patient. Once the robotic arm is in the desired position, the arm is fixed to maintain the desired trajectory. The tool holder serves as a stable, secure guide through which a tool may be moved through or slid at an accurate angle. Thus, the disclosed technology provides the surgeon with reliable instruments and techniques to successfully perform his/her surgery.

In some embodiments, the operation may be spinal surgery, such as a discectomy, a foraminotomy, a laminectomy, or a spinal fusion. In some implementations, the surgical robotic system includes a surgical robot 102 on a mobile cart. The surgical robot 102 may be positioned in proximity to an operating table 112 without being attached to the operating table, thereby providing maximum operating area and mobility to surgeons around the operating table and reducing clutter on the operating table. In alternative embodiments, the surgical robot (or cart) is securable to the operating table. In certain embodiments, both the operating table and the cart are secured to a common base to prevent any movement of the cart or table in relation to each other, even in the event of an earth tremor.

The mobile cart may permit a user (operator) 106a, such as a technician, nurse, surgeon, or any other medical personnel in the operating room, to move the surgical robot 102 to different locations before, during, and/or after a surgical procedure. The mobile cart enables the surgical robot 102 to be easily transported into and out of the operating room 100. For example, a user 106a may move the surgical robot into the operating room from a storage location. In some implementations, the mobile cart may include wheels, a track system, such as a continuous track propulsion system, or other similar mobility systems for translocation of the cart. The mobile cart may include an attached or embedded handle for locomotion of the mobile cart by an operator.

For safety reasons, the mobile cart may be provided with a stabilization system that may be used during a surgical procedure performed with a surgical robot. The stabilization mechanism increases the global stiffness of the mobile cart relative to the floor in order to ensure the accuracy of the surgical procedure. In some implementations, the wheels include a locking mechanism that prevents the cart from moving. The stabilizing, braking, and/or locking mechanism may be activated when the machine is turned on. In some implementations, the mobile cart includes multiple stabilizing, braking, and/or locking mechanisms. In some implementations, the stabilizing mechanism is electro-mechanical with electronic activation. The stabilizing, braking, and/or locking mechanism(s) may be entirely mechanical. The stabilizing, braking, and/or locking mechanism(s) may be electronically activated and deactivated.

In some implementations, the surgical robot 102 includes a robotic arm mounted on a mobile cart. An actuator may move the robotic arm. The robotic arm may include a force control end-effector configured to hold a surgical tool. The robot may be configured to control and/or allow positioning and/or movement of the end-effector with at least four degrees of freedom (e.g., six degrees of freedom, three translations and three rotations).

In some implementations, the robotic arm is configured to releasably hold a surgical tool, allowing the surgical tool to be removed and replaced with a second surgical tool. The system may allow the surgical tools to be swapped without re-registration, or with automatic or semi-automatic re-registration of the position of the end-effector.

In some implementations, the surgical system includes a surgical robot 102, a tracking detector 108 that captures the position of the patient and different components of the surgical robot 102, and a display screen 110 that displays, for example, real time patient data and/or real time surgical robot trajectories.

In some implementations, a tracking detector 108 monitors the location of patient 104 and the surgical robot 102. The tracking detector may be a camera, a video camera, an infrared detector, field generator and sensors for electromagnetic tracking or any other motion detecting apparatus. In some implementation, based on the patient and robot position, the display screen displays a projected trajectory and/or a proposed trajectory for the robotic arm of robot 102 from its current location to a patient operation site. By continuously monitoring the patient and robotic arm positions, using tracking detector 108, the surgical system can calculate updated trajectories and visually display these trajectories on display screen 110 to inform and guide surgeons and/or technicians in the operating room using the surgical robot. In addition, in certain embodiments, the surgical robot 102 may also change its position and automatically position itself based on trajectories calculated from the real time patient and robotic arm positions captured using the tracking detector 108. For instance, the trajectory of the end-effector can be automatically adjusted in real time to account for movement of the vertebrae or other part of the patient during the surgical procedure.

Figure 2:
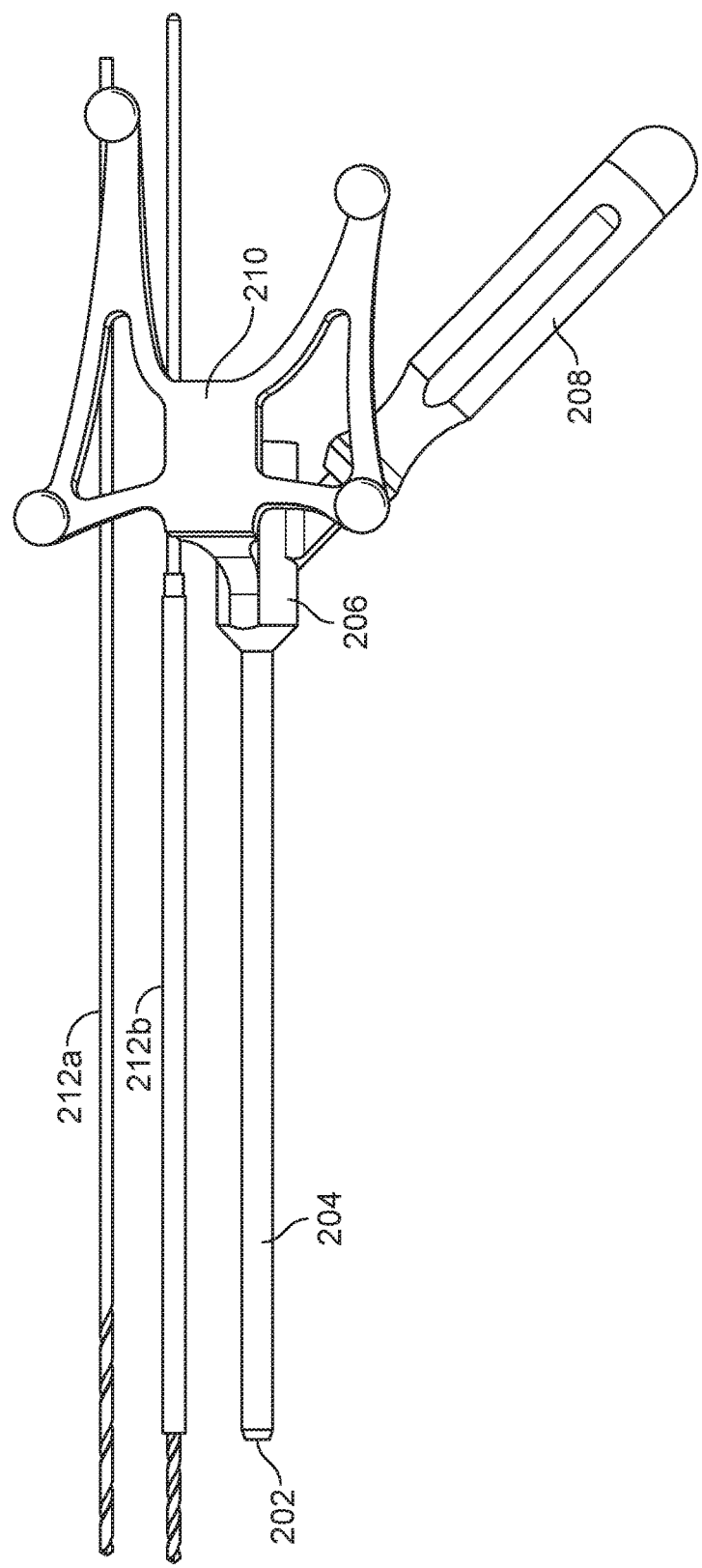
FIG. 2 is an illustration of an example drill guide and two drill bits.

FIG. 2 is an illustration of an example drill guide and two drill bits. In some implementations, the surgical instrument held by the instrument holder is an instrument guide (e.g., drill guide) configured to receive a second surgical instrument therethrough. The second surgical instrument may be a drill bit, tap, screw driver, or awl.

In some implementations, an instrument holder is an interface between the robotic arm and a surgical instrument used during surgery. The instrument holder may be configured to hold the surgical instrument precisely, rigidly, and in a stable manner while permitting a surgeon to easily and quickly install, or withdraw the surgical instrument in case of emergency. The surgical instrument may be an instrument guide such as the drill guide 202 shown in FIG. 2. In this example, the drill guide 202 includes a hollow tube 204 with a reinforcement 206 at one end. A handle 208 and/or a navigation marker 210 may be attached (removably or permanently) to the reinforcement 206. The navigation marker may be, for example, navigation tracker such as the Dedicated NavLock™ tracker from Medtronic, Inc. of Minneapolis, Minn. Drill bits 212a-b may be used with the drill guide 202 to perform an operation, such as preparing holes in vertebrae.

Figure 3A:
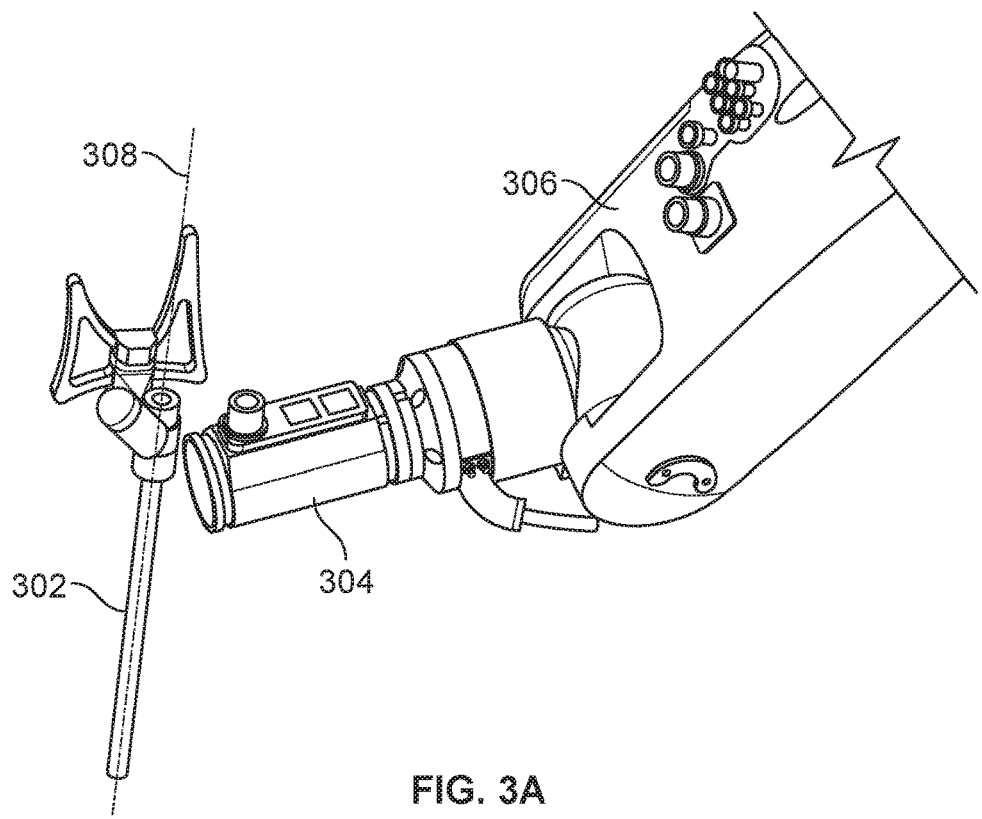
FIG. 3A is an illustration of a drill guide in the position in which it is held relative to the robotic arm.
Figure 3B:
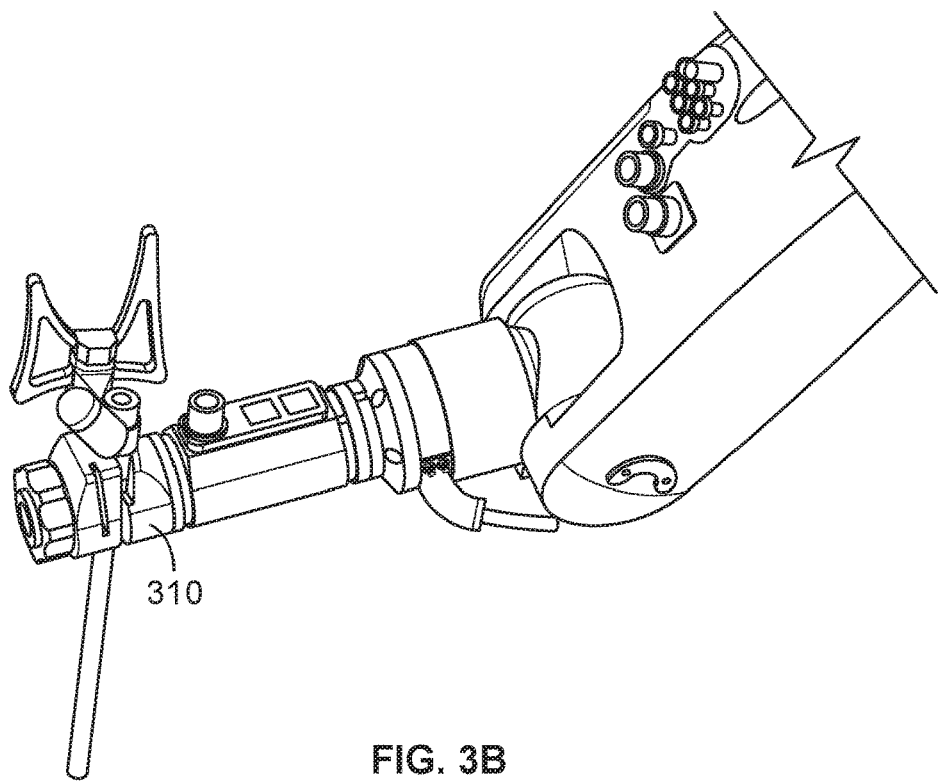
FIG. 3B is an illustration of a drill guide held by an example instrument holder.

FIG. 3A is an illustration of a drill guide 302 in the position in which it is held relative to a tool holder's body 304. The tool holder 304 is attached to the robotic arm 306. The term tool holder is a generic term used to designate, in some implementations, the entire device that is attached to the robot arm's tip. FIG. 3B is an illustration of a drill guide held by an example instrument holder that includes, among other things, a base 310.

Figure 4:
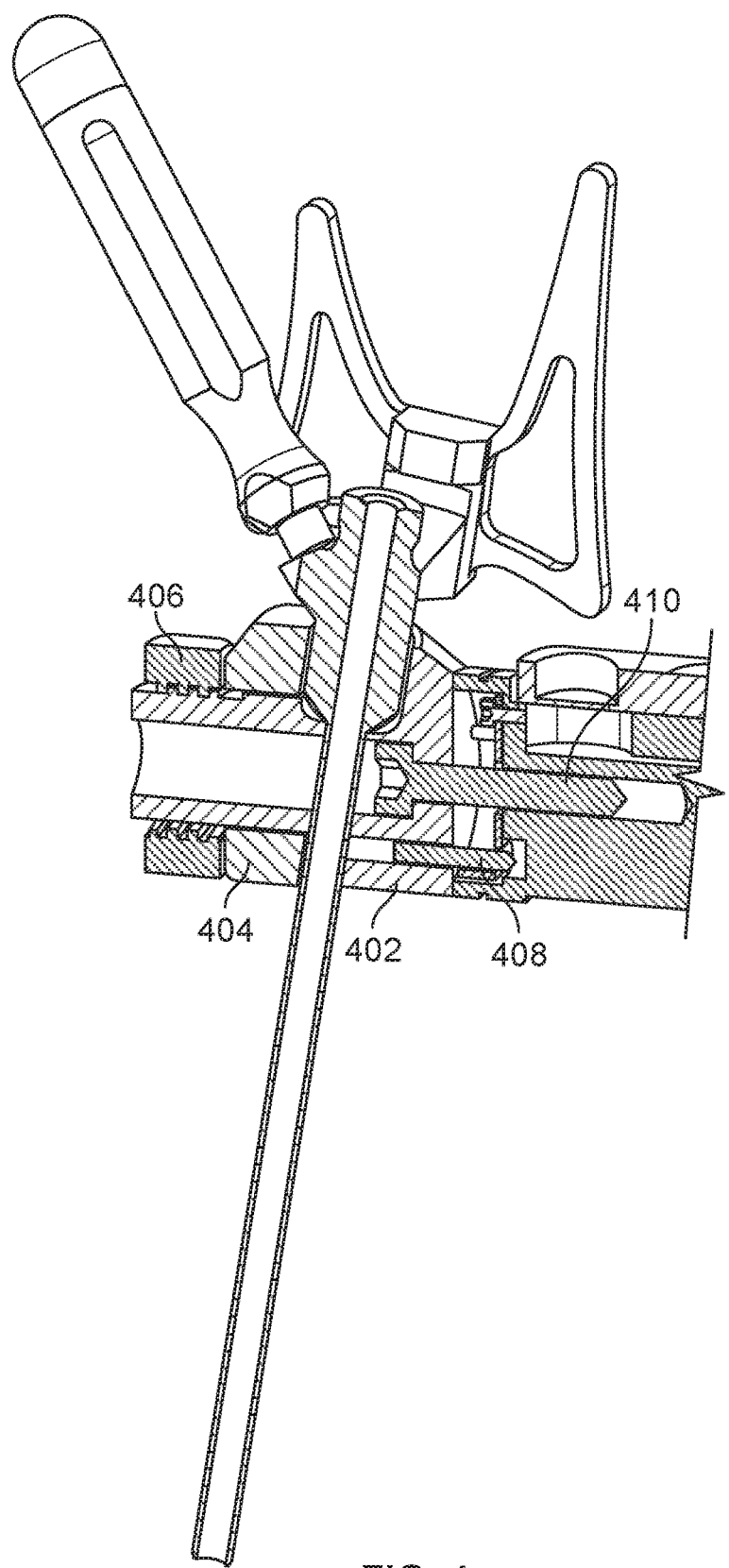
FIG. 4 is an illustration of a cross-sectional view an example instrument holder with a drill guide held therein.

FIG. 4 is an illustration of a cross-sectional view of an example instrument holder with a drill guide held therein. In some implementations, the instrument holder includes a base 402, a clamp 404, a nut 406, localization pins 408 (e.g., three localization pins), and a tightening screw 410. The base 402 is configured to be mechanically coupled to the robotic arm via a screw 410 inserted in a channel of the base 402. The base 402 includes a second channel through which a surgical instrument (e.g., a drill guide) may be placed. The nut 406 may be tightened to securely hold the surgical instrument between the clamp 404 and the base 402.

Figure 5B:
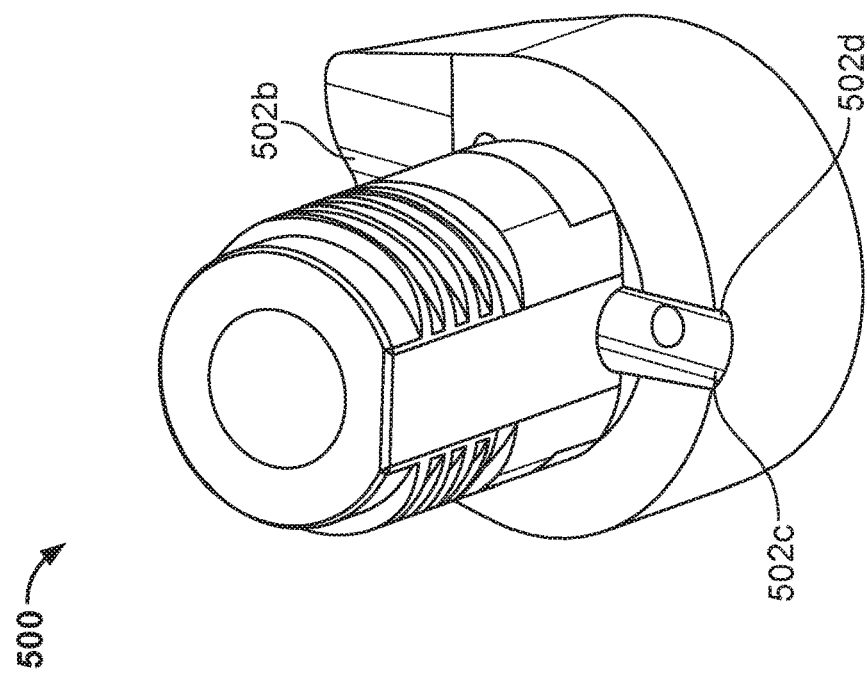
FIGS. 5A-B are illustrations of an example base of a surgical instrument holder.
Figure 5A:
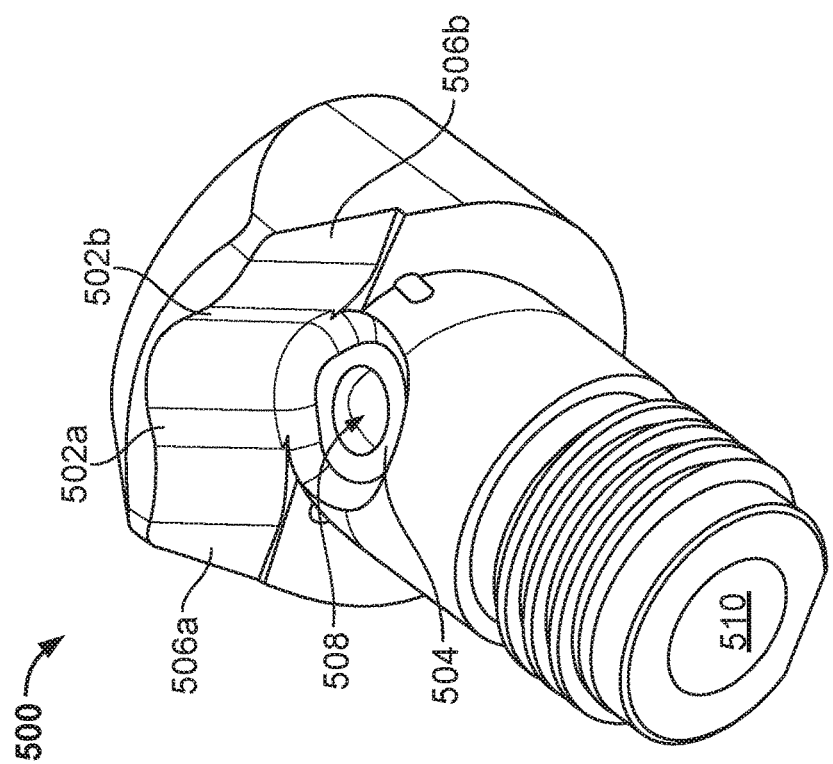

FIGS. 5A-B are illustrations of an example base 500 of a surgical instrument holder. The base may include two surfaces (502a-b) (e.g., forming a large "V"—shown in blue in FIG. 5A) allowing localizing of the instrument guide precisely as well as in a stable manner. The surfaces 502a and 502b may be flat or curved surfaces. The large "V" in the upper portion of the base (e.g., surfaces 502a-b) may receive the cylindrical reinforcement portion of the guide (e.g., 206 in FIG. 2) while another small "V" (shown by 502c-d) receives the external cylindrical tube portion of the guide (e.g., 204 in FIG. 2). Surface 504 may define an axial position of the instrument guide. Surface 506a and/or 506b may come in contact with a navigation marker's attachment mechanism to prevent the instrument from rotating along its axis when assembled. In some implementations, the base and the surgical instrument are configured such that only surfaces 502, 504, and 506 come in contact with the surgical instrument when inserted therein. This may allow the surgical instrument to be fully constrained in space.

The base 500 may include a first channel 510 having an interior surface sized and shaped to accommodate a tightening screw configured to securely attach the base 500 directly or indirectly (e.g., via a tool holder) to a robotic arm of the robotic surgical system. The tightening screw may be placed inside the first channel 510 and extend through the opposite side of the base where it engages the robotic arm (e.g., threads).

The base 500 may include a second channel 508 having an interior surface with a tapered cylindrical shape sized to accommodate a surgical instrument therethrough such that movement of the surgical instrument is constrained in all directions except along an axis defined by the second channel surface 508. The first channel 510 and the second channel 508 may intersect.

Figure 6A:
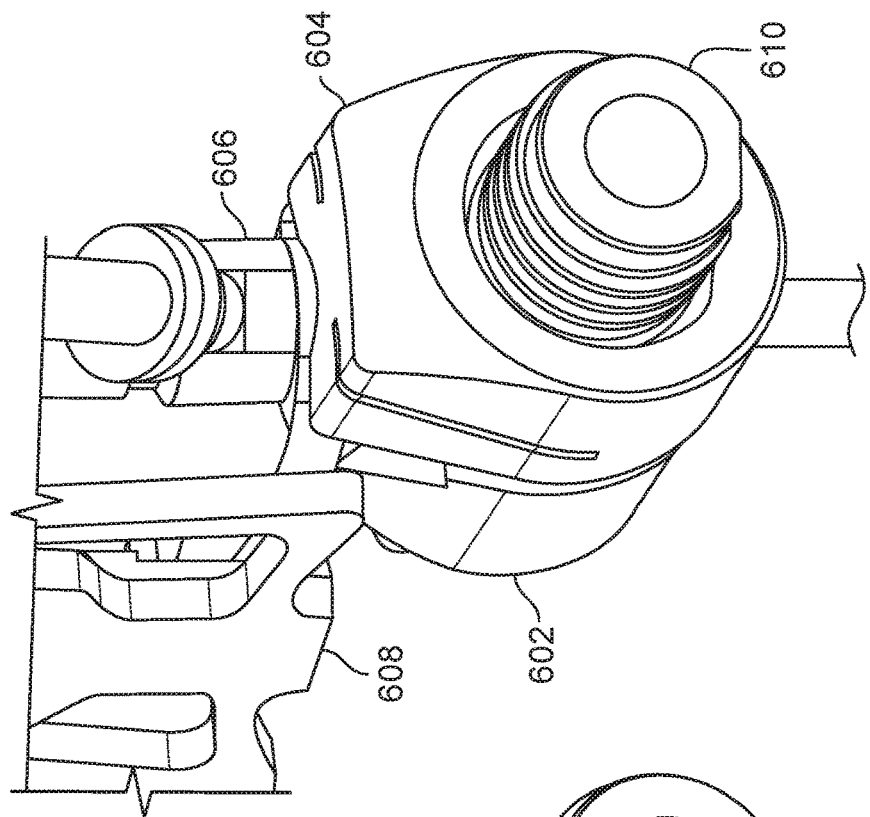
FIG. 6A is an illustration of an example surgical instrument holder before a clamp is installed.
Figure 6B:
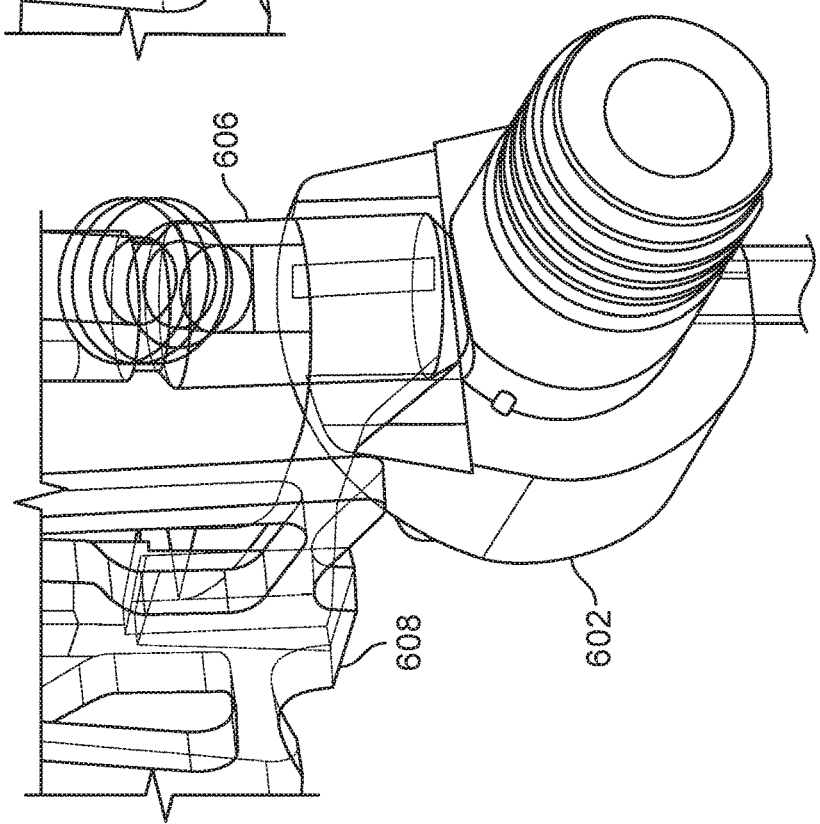
FIG. 6B is an illustration of an example surgical instrument holder with a clamp inserted and positioned against the instrument.
Figure 9A:
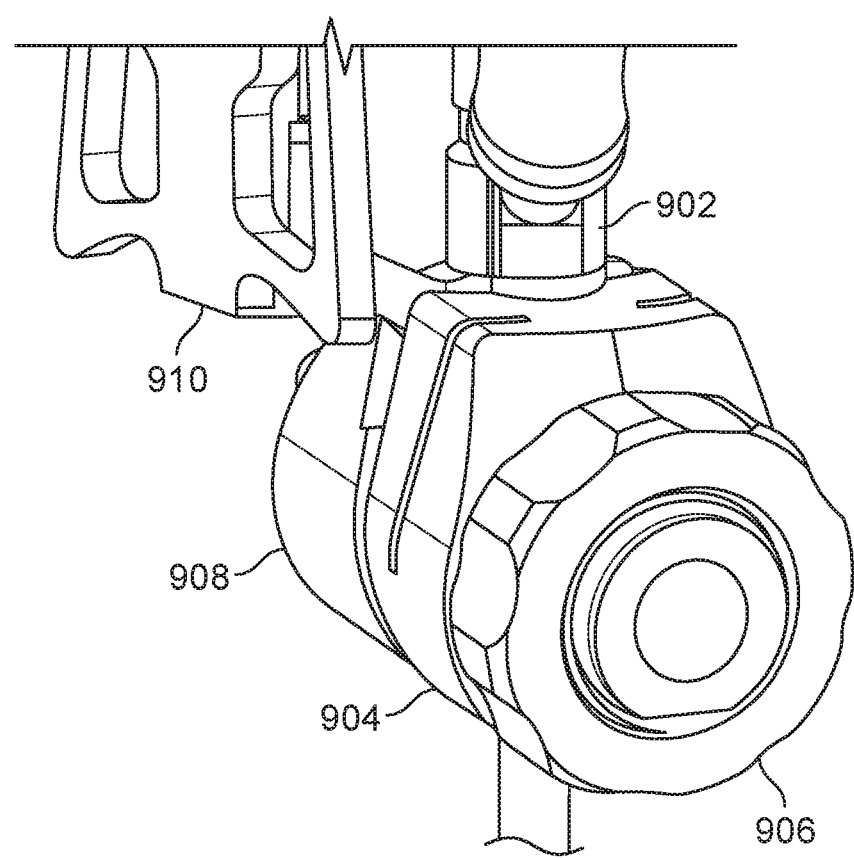
FIGS. 9A-B are illustrations of an example instrument holder with an instrument and a nut for securing the instrument in the holder.

FIG. 6A is an illustration of an example surgical instrument holder before a clamp is installed. FIG. 6B is an illustration of an example surgical instrument holder with a clamp inserted and positioned against the instrument. The clamp 604 may be configured to engage the surgical instrument 606 and/or a navigation marker 608 when the surgical instrument 606 is placed through the second channel such that the surgical instrument is securely held between the clamp 604 and the base 602 upon tightening of a nut (e.g., nut 906 as shown in FIG. 9A). The clamp 604 may include a channel having an interior surface shaped and sized to accommodate the first channel 610 sliding therethrough.

Figure 7:
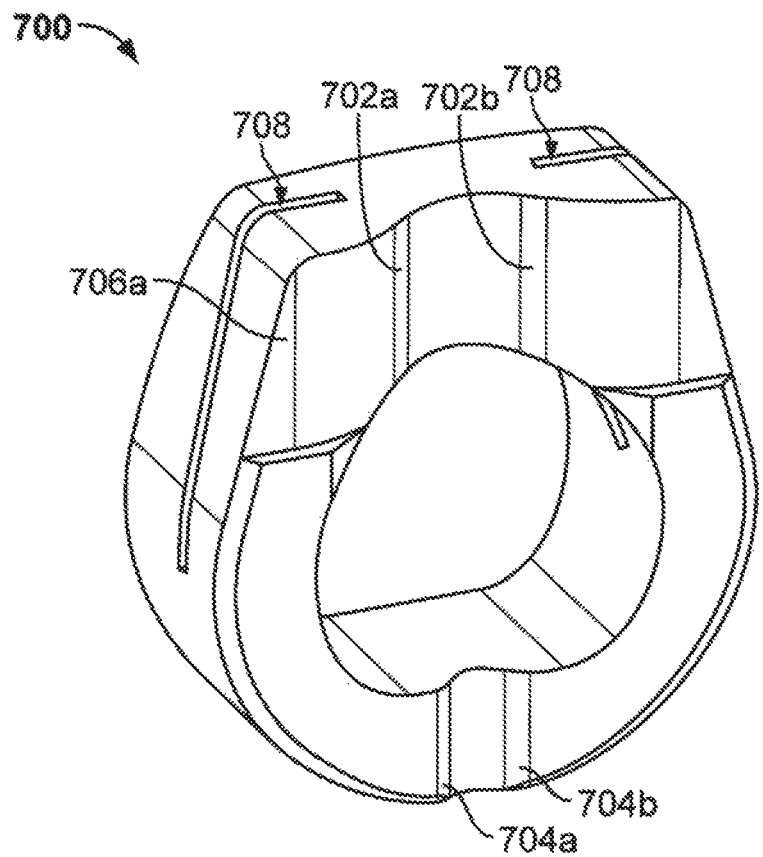
FIG. 7 is an illustration of an example clamp from the guide-side of the clamp.

FIG. 7 is an illustration of an example clamp 700 from the guide-side of the clamp 700. The clamp 700 may include one or more tapered curved surface (e.g., 702 & 704) configured to be engaged by a surgical instrument when the surgical instrument is secured in the second channel (e.g., 508 as shown in FIG. 5A). The tapered curved surface may include four surfaces 702a-b and 704a-b (e.g., four flat surfaces) forming two "V" shapes (shaded) that come in contact with the surgical instrument when inserted in the second channel (e.g., 508 as shown in FIG. 5A). Surfaces 706a and/or 706b may come in contact with the navigation marker's attachment to hold it between the clamp 700 and the base (e.g., 500 in FIG. 5A). In some implementations, the navigation marker may be mounted in two different orientations, one in which it contacts surface 706a and another in which it contacts surface 706b when the surgical instrument is inserted in the second channel. The clamp 700 may include one or more slits 708 configured to allow a body of the clamp to elastically deform upon tightening of the nut. This may compensate for dimension variations in, among other things, surgical tools inserted into the surgical instrument holder.

Figure 8:
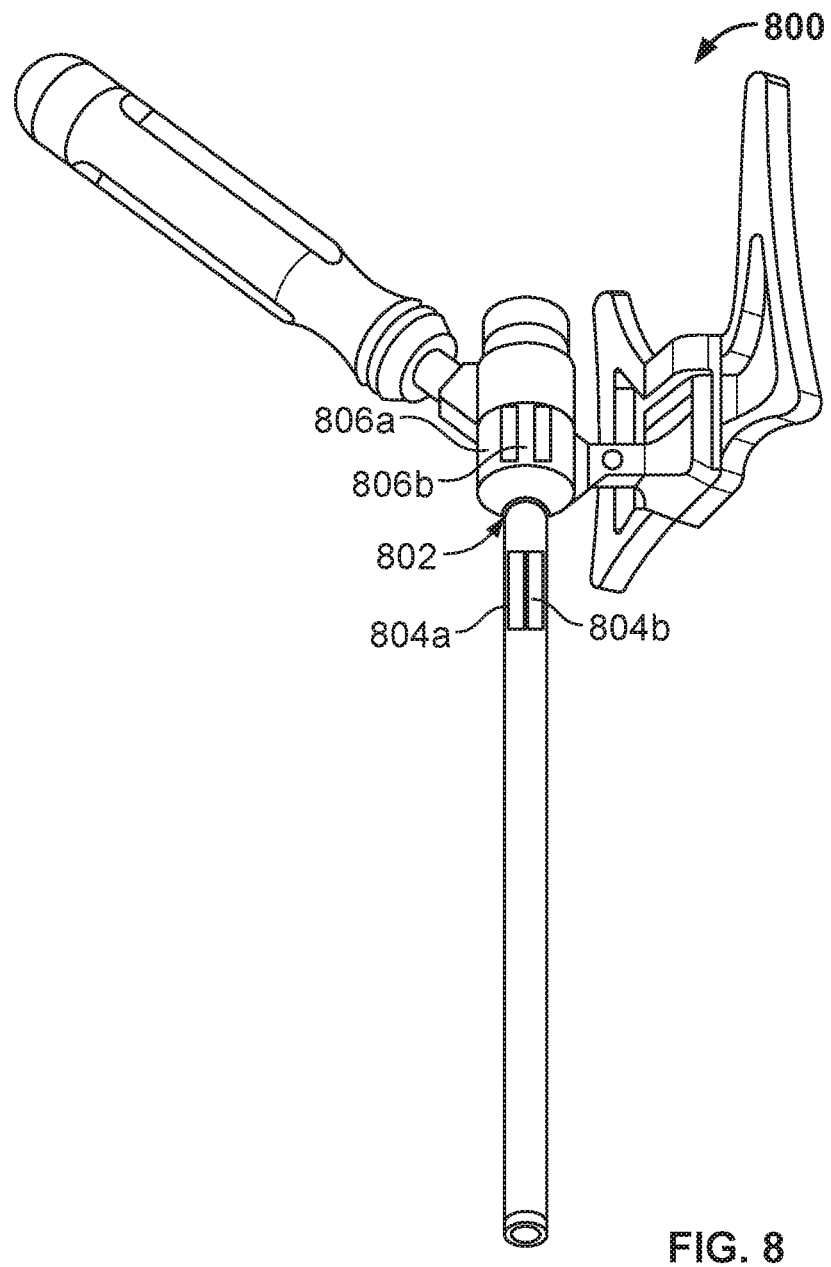
FIG. 8 is an illustration of an example surgical instrument.

FIG. 8 is an illustration of an example surgical instrument 800. The surfaces of the surgical instrument that contact the surgical instrument holder are shown in FIG. 8. In some implementations, surface 802 of the surgical instrument contacts surface 504 of the surgical instrument holder 500 as shown in FIG. 5A when the surgical instrument holder is inserted in the second channel (e.g., 508 in FIG. 5A). In some implementations, surface 806a-b of the surgical instrument contacts surface 502a-b of the surgical instrument holder 500 as shown in FIG. 5A when the surgical instrument holder is inserted in the second channel (e.g., 508 in FIG. 5A). In some implementations, surface 804a-b of the surgical instrument contacts surface 502c-d of the surgical instrument holder 500 as shown in FIG. 5A when the surgical instrument holder is inserted in the second channel (e.g., 508 in FIG. 5A). This configuration may allow for a very stable holding of the instrument in the holder. Additionally, this configuration may prevent a user from inserting the clamp in a wrong orientation with respect to the base (e.g., given the difference in size and/or shape of surface 804 and 806 where the clamp contacts the instrument).

Figure 9B:
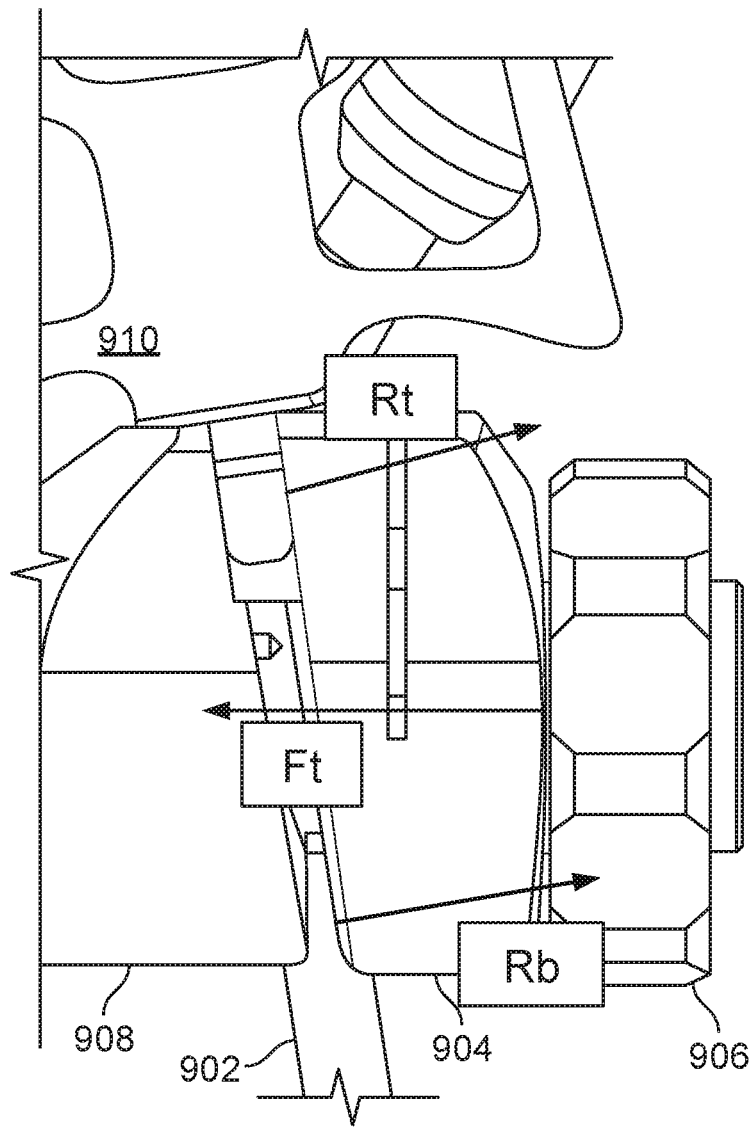

FIGS. 9A-B are illustrations of an example instrument holder with an instrument 902 and a nut 906 for securing the instrument 902 in the holder. An instrument 902 may be secured between a base 908 and a clamp 904. In some implementations, a navigation marker 910 is secured between the base 908 and the clamp 904. A nut 906 may be tightened against the clamp 904 to press the instrument 902 (and/or navigation marker 910) securely between the clamp 904 and the base 908. The nut 906 may be configured to engage threads on an exterior surface of the first channel (e.g., 510 as shown in FIG. 5A) and a cambered surface of the clamp.

In order to balance the tightening force Ft of the nut 906 between the bottom reaction force Rb and the top reaction force Rt as illustrated in FIG. 9B, the nut 906, in some implementations, comes in contact with a cambered surface on the clamp 904 forming only a horizontal line of contact instead of a full surface. This horizontal line of contact may allow the clamp 904 to slightly tilt to accommodate for dimensional variations. This isostatic designs may allow for decreasing internal forces and thus optimizing tightening force Rt and Rd.

The navigation marker may be, for example, a navigation tracker such as the Dedicated NavLock™ tracker from Medtronic, Inc. of Minneapolis, Minn. The navigation marker may be used by a navigation camera to track the surgical instrument. In some implementations, a computing system of the robotic surgical system tracks the position of the patient and the surgical tool, for example using tracking module. The computing system receives images of the patient, surgical tool position, and end effector positions from a tracking detector. In some implementations, images of the patient are received from a digital 3D scanner. Tracking module, for example, may calculate the position of the surgical tool and the patient in real time. In an implementation, tracking module may track the position of the surgical tool and the patient in free space. In another implementation, tracking module may track the position of the surgical tool and the patient with relation to each other. In an implementation tracking module may identify, from the images received from the tracking detector, the portion of the patient to be operated on and the surgical tool and track these identified objects. In another implementation, tracking module may track markers (e.g., navigation markers attached to the portion of the patient to be operated on and the surgical tool. Tracking module may identify the markers from images received from tracking detector and identify that these markers are attached to the patient and to the surgical tool and accordingly, track the patient position and surgical tool position.

Figure 10A:
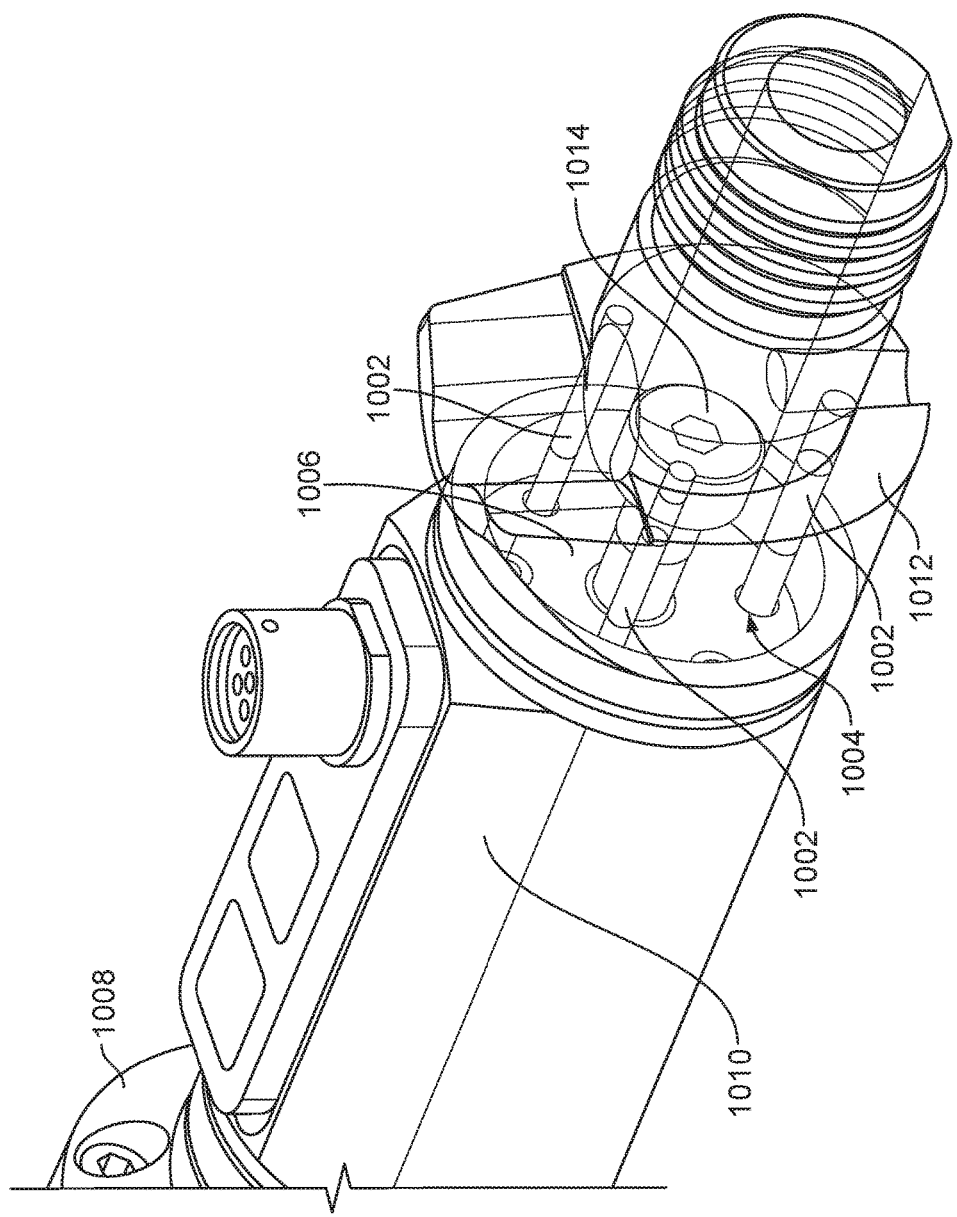

FIGS. 10A-B are illustrations of a system for securing the instrument holder on the robotic arm. In some implementations, the instrument holder needs to be sterilized (e.g., in autoclave). The disclosed instrument holder may be easily installed and removed from the robotic system without deteriorating localization precision as well as attachment rigidity. Localization precision may be achieved by, for example, three localization pins 1002 inserted into the base. A different number of localization pins 1002 may be used (e.g., 1 to 5 pins). The pins 1002 may come in contact with oblong openings 1004 in a thin localization plate 1006 precisely held on the robotic arm 1008 (e.g., held on the tool holder's body 1010). The instrument holder's base 1012 may be localized on the robotic arm 1008 (e.g., held on the tool holder's body 1010) using pins 1002 that come in contact with oblong openings 1004 in a localization plate 1006 precisely held on the robot 1008. A screw 1014 may be tightened directly into the robot 1008 to rigidly attached the instrument holder's base 1012 to the robot 1008. FIG. 10B illustrates a front view of an example localization plate 1006. The one or more pins 1002 may be inserted into the base such that the one or more pins 1002, upon mechanically coupling the base to the robotic arm, engage one or more openings 1004 in a robotic arm 1008 (e.g., in a localization plate 1006 of the robotic arm 1008) thereby precisely locating the surgical instrument holder relative to the robotic arm 1008 (e.g., the one or more openings 1004 may be wider than the one or more pins and the one or more openings may taper long their lengths).

Figure 11:
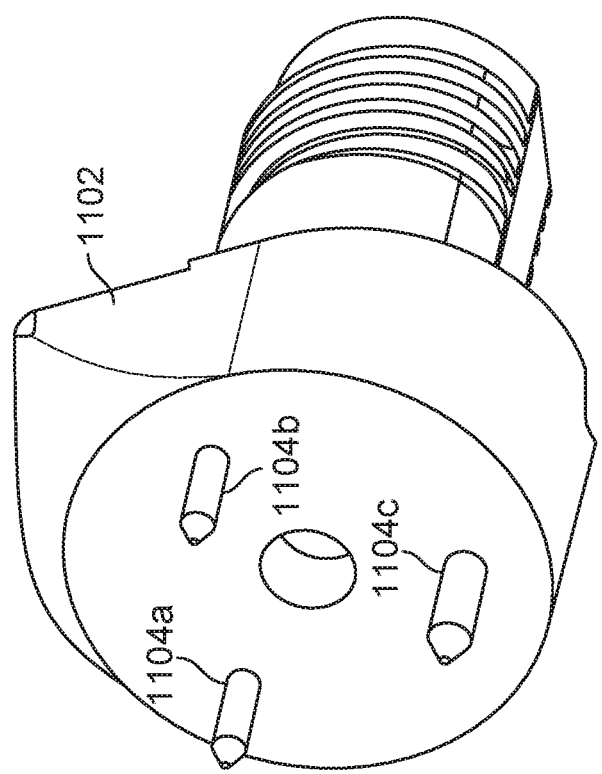
FIG. 11 is an illustration of an example base of an instrument holder.

FIG. 11 is an illustration of an example base 1102 of an instrument holder with pins 1104a-c inserted into the base 1102. The base 1102 may be configured to be mechanically coupled to a robotic arm of the robotic surgical system. The base 1102 may include one or more pins 1104 (e.g., three pins 1104*a-c*) inserted into the base 1102 such that the one or more pins 1104, upon mechanically coupling the base 1102 to the robotic arm, engage one or more openings in a tool support (e.g., in a localization plate of the robotic arm) thereby precisely locating the surgical instrument holder relative to the robotic arm.

Figure 12A:
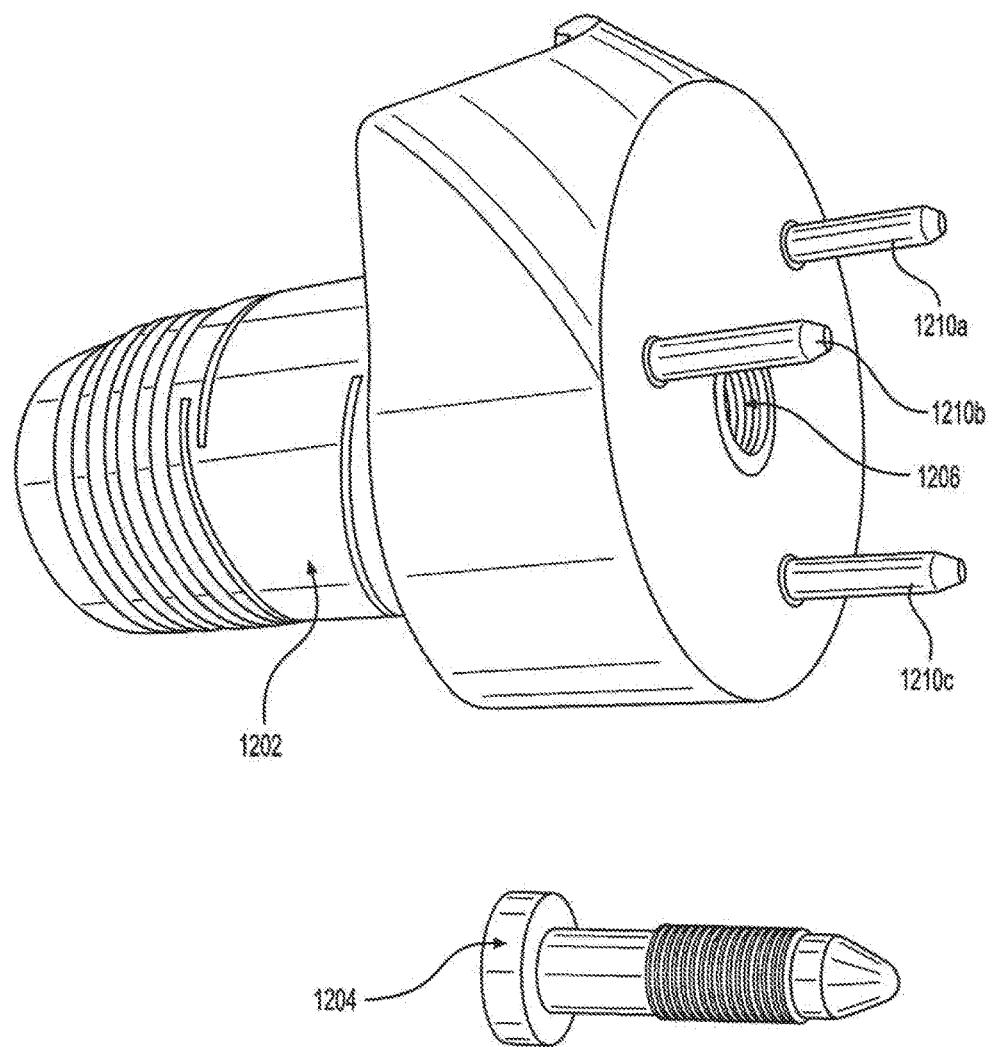
FIG. 12A is an illustration of a clamp base and torque screw, in accordance with an embodiment of the invention.

FIG. 12A is an illustration of a clamp base 1202 and torque screw 1204. In some implementations, a threaded bushing 1206 is press fitted into the clamp base 1202. The torque screw 1204 is made of metal such that it provides a strong attachment to the robot and satisfies the cleaning and sterilization requirements. The threads on the torque screw 1204 engage the threaded bushing 1206 that is press fitted into the clamp base 1202. As the torque screw 1204 is tightened, the threads on the torque screw 1204 pass through the threaded bushing 1206 such that the end of the torque screw 1204 closest to the torque screw head (i.e., the portion that has a smaller diameter and no threads) resides in the threaded bushing 1206 (e.g., somewhat loosely since there are no threads). The advantage here is the torque screw 1204 and clamp base assembly 1202 can then be mounted on the robot without the risk of losing the torque screw 1204 during assembly as the torque screw 1204 cannot slide out of the threaded bushing 1206 as the threads on the torque screw 1204 will contract the threaded bushing 1206 (i.e., thereby preventing the torque screw 1204 from sliding out of the bushing 1206 without unscrewing the torque 1204 from the bushing 1206). The clamp base 1202 in this example includes three localization pins 1210*a-c* as described above.

Figure 12B:
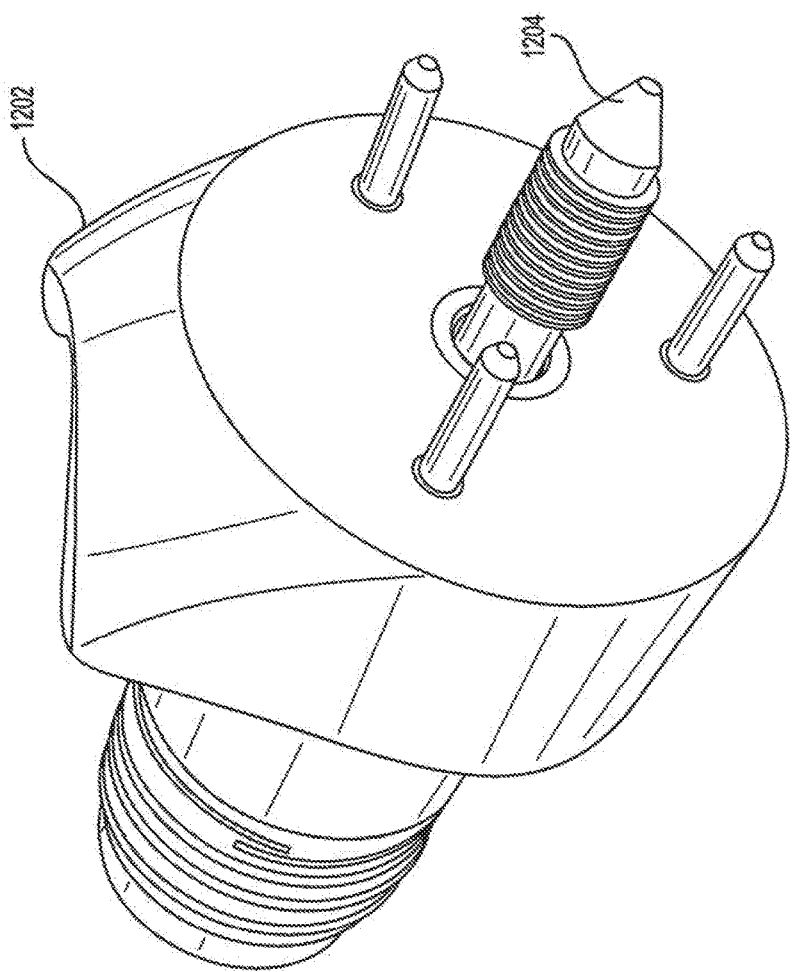
FIG. 12B is an illustration of a clamp base and torque screw, in accordance with an embodiment of the invention.

FIG. 12B is an illustration of a clamp base 1202 with a torque screw 1204 fully inserted into the threaded bushing 1206. The end of the torque screw 1204 has a smaller diameter in order to allow tightening it on the tool holder body as well as providing a gap between the torque screw 1204 and clamp base 1202 for cleaning.

Figure 12C:
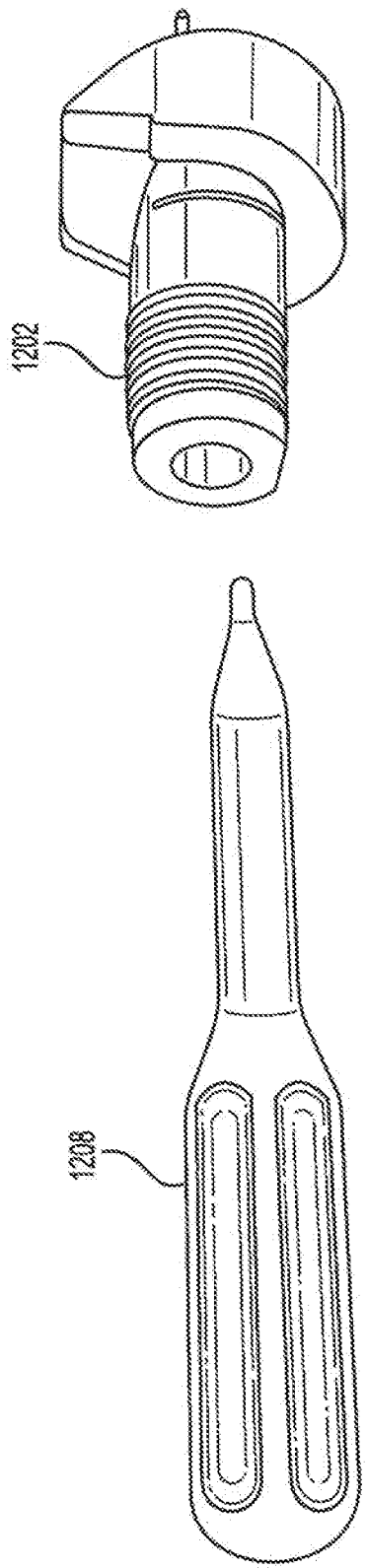
FIG. 12C is an illustration of a clamp base and screw driver, in accordance with an embodiment of the invention.

FIG. 12C is an illustration of a clamp base 1202 and screw driver 1208. For tightening the torque screw 1204, a screw driver 1208 is designed with a shaft diameter close to the inner diameter of the clamp base 1202. Therefore, the screw driver 1208 is guided by the clamp base 1202 once it's inserted into the clamp base 1202 and this simplifies fitting the tip of the screwdriver 1208 on the head of the screw 1204.

In view of the structure, functions and apparatus of the systems and methods described here, in some implementations, a system and method for performing surgery with a robotic surgical system are provided. Having described certain implementations of methods and apparatus for supporting a robotic surgical system, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the disclosed technology that consist essentially of, or consist of, the recited components, and that there are processes and methods according to the disclosed technology that consist essentially of, or consist of, the recited processing steps.

It should be understood that the order of steps or order for performing certain action is immaterial so long as the disclosed technology remains operable. Moreover, two or more steps or actions may be conducted simultaneously.

What is claimed is:

1. A robotic surgical system comprising:
a surgical robot mounted on a mobile cart, the surgical robot having a moveable robotic arm and a tool holder attached to the robotic arm,
wherein the tool holder includes a base configured to be mechanically coupled to the robotic arm, the base having a first channel sized and shaped to accommodate a tightening screw configured to securely attach the base directly or indirectly to the robotic arm and a second channel sized and shaped to accommodate a surgical instrument therethrough, wherein the first channel intersects the second channel.

2. The robotic surgical system of claim 1, wherein movement of the surgical instrument is constrained in all directions except along an axis defined by the second channel.

3. The robotic surgical system of claim 1, wherein the tool holder further comprises one or more pins projecting from the base such that the one or more pins are configured to engage one or more openings in the robotic arm thereby precisely locating the tool holder relative to the robotic arm.

4. The robotic surgical system of claim 3, wherein the one or more openings are one or more oblong openings.

5. The robotic surgical system of claim 3, wherein the one or more openings are wider than the one or more pins and the one or more openings taper long their lengths.

6. The robotic surgical system of claim 1, wherein the tool holder further comprises a clamp configured to engage the surgical instrument when placed through the second channel such that the surgical instrument is securely held between the clamp and the base.

7. The robotic surgical system of claim 6, wherein the clamp comprises a third channel having an interior surface shaped and sized to accommodate the first channel sliding therethrough; a second tapered curved surface configured to be engaged by a surgical instrument when the surgical instrument is secured in the second channel; and one or more slits configured to allow a body of the clamp to elastically deform upon tightening of a nut, wherein the nut is configured to engage threads on an exterior surface of the first channel and a cambered surface of the clamp.

8. The robotic surgical system of claim 7, wherein instrument holder is configured such that a navigation marker is securely held between the clamp and the base upon placing the navigation marker between the clamp and the base and tightening the nut.

9. The robotic surgical system of claim 7, wherein an exterior surface of the first channel is threaded to securely accommodate the nut such that surgical instrument is securely held between the clamp the base upon placing the surgical instrument in the second channel and tightening the nut.

10. The robotic surgical system of claim 1, wherein the base comprises a threaded bushing having an interior surface.

11. The robotic surgical system of claim 10, wherein the first channel passes through an interior surface of the threaded bushing and the interior surface of the threaded bushing is threaded such that the threads on the tightening screw engage the threads on the threaded bushing as the tightening screw is inserted through the threaded bushing.

12. The robotic surgical system of claim 1, wherein the tightening screw comprises a tip on a proximate end of a screw body, a head on a distal end of the screw body, and threads along a portion of the screw body.

13. The robotic surgical system of claim 12, wherein the threads are along a portion of the screw body closest to the tip of the tightening screw.

14. The robotic surgical system of claim 13, wherein the portion of the screw body closest to the head is smooth such that the tightening screw is loosely held in place by the threaded bushing when the tightening screw is fully inserted into the threaded bushing.

15. The robotic surgical system of claim 1, wherein the surgical instrument is an instrument guide configured to receive a second surgical instrument therethrough, the second surgical instrument comprising a member selected from the group consisting of: a drill bit, tap, screw driver, and awl.

16. The robotic surgical system of claim 1, wherein the robotic surgical system is for use in spinal surgery.

17. A robotic surgical system comprising:
a surgical robot mounted on a mobile cart, the surgical robot having a moveable robotic arm and a tool holder attached to the robotic arm,
wherein the tool holder includes a base configured to be mechanically coupled to the robotic arm, the base having a first channel sized and shaped to accommodate a tightening screw configured to securely attach the base directly or indirectly to the robotic arm and a second channel sized and shaped to accommodate a surgical instrument therethrough, wherein the first channel intersects the second channel, and
the tool holder further comprising one or more pins projecting from the base such that the one or more pins are configured to engage one or more openings in the robotic arm thereby precisely locating the tool holder relative to the robotic arm.

18. The robotic surgical system of claim 17, wherein the one or more openings are wider than the one or more pins and the one or more openings taper long their lengths.

19. The robotic surgical system of claim 17, wherein the tool holder further comprises a clamp configured to engage the surgical instrument when placed through the second channel such that the surgical instrument is securely held between the clamp and the base.

20. The robotic surgical system of claim 19, wherein the clamp comprises a third channel having an interior surface shaped and sized to accommodate the first channel sliding therethrough; a second tapered curved surface configured to be engaged by a surgical instrument when the surgical instrument is secured in the second channel; and one or more slits configured to allow a body of the clamp to elastically deform upon tightening of a nut, wherein the nut is configured to engage threads on an exterior surface of the first channel and a cambered surface of the clamp.

* * * * *